(12) United States Patent
Bodlaender et al.

(10) Patent No.: US 7,927,559 B2
(45) Date of Patent: Apr. 19, 2011

(54) ASSAY DEVICE

(75) Inventors: Maarten Peter Bodlaender, Eindhoven (NL); Wilhelmus Gijsbert Johannes Joseph Stut, Eindhoven (NL); Erik Petrus Nicolaas Damen, Doorwerth (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 137 days.

(21) Appl. No.: 12/299,680

(22) PCT Filed: May 2, 2007

(86) PCT No.: PCT/IB2007/051620
§ 371 (c)(1),
(2), (4) Date: Nov. 5, 2008

(87) PCT Pub. No.: WO2007/132376
PCT Pub. Date: Nov. 22, 2007

(65) Prior Publication Data
US 2009/0104074 A1    Apr. 23, 2009

(30) Foreign Application Priority Data

May 9, 2006 (EP) .................................... 06113708
Jun. 28, 2006 (EP) .................................... 06116196

(51) Int. Cl.
*G01N 21/00* (2006.01)
*G01D 11/24* (2006.01)
*A61B 5/00* (2006.01)
*G06F 11/00* (2006.01)

(52) U.S. Cl. ............... 422/401; 73/431; 702/188; 705/3
(58) Field of Classification Search ................. 422/401; 73/431; 705/3; 702/188
See application file for complete search history.

(56) References Cited

U.S. PATENT DOCUMENTS

| 5,395,504 | A | 3/1995 | Saurer et al. |
| 5,580,794 | A | 12/1996 | Allen |
| 6,352,863 | B1 | 3/2002 | Guirguis |
| 2002/0086294 | A1 | 7/2002 | Ellson et al. |
| 2004/0248106 | A1 | 12/2004 | Leonard et al. |
| 2008/0053222 | A1* | 3/2008 | Ehrensvard et al. ............ 73/431 |
| 2009/0132204 | A1* | 5/2009 | Bodlaender et al. .......... 702/188 |
| 2009/0192820 | A1* | 7/2009 | Bodlaender et al. ............. 705/2 |

FOREIGN PATENT DOCUMENTS

| CA | 2516490 A1 | 5/2004 |
| CH | 603136 A | 8/1978 |
| DE | 69634490 T2 | 3/2006 |
| EP | 0972196 B1 | 1/2000 |
| WO | 9506240 A | 3/1995 |
| WO | 9533996 A1 | 12/1995 |
| WO | 2004044571 A1 | 5/2004 |

OTHER PUBLICATIONS

Picraux S T et al: "Micromachining Mechanical, Chemical, and Optical Components onto the Same Wafers as Electronic Circuits Produces Powerful Systems That can Understand and Influence Their Environments" IEEE Inc. New York, US, vol. 35, No. 12, Dec. 1998, pp. 24-33, XP000875830 ISSN: 0018-9235.

* cited by examiner

*Primary Examiner* — Lore Jarrett

(57) ABSTRACT

A disposable assay device that assays one or more samples, and transmits assay data or information to a remote receiving system. The device is provided with one or more assay context sensors configured to monitor one or more assay context factors.

20 Claims, 6 Drawing Sheets

ASSAY DEVICE

FIELD OF THE INVENTION

The invention relates to a disposable assay device configured to assay one or more samples, and configured for transmitting assay data or information to a remote receiving system.

BACKGROUND OF THE INVENTION

International patent application WO 95/33996, of Zwanziger et. al., discloses a home test kit for use in testing for a disease or a physiological condition, with telephone verification of test results. The known home test kit facilitates the delivery of any necessary counseling as a result of the outcome of a test. During use, an individual can obtain a sample of physiological fluid from him or herself. The sample can be introduced into an assay device to produce a coded pattern indicative of the presence or absence of the disease. The individual can transmit the coded pattern to a remote location for interpretation, for example by telephone. Then, the individual can receive, from the remote location, an interpretation of the coded pattern together with any counseling which may be appropriate in view of the interpretation of the coded pattern. In this way, the remote location has to be used for interpretation of the test.

Also, from EP972196B1 a different assessment device is known, where a recording part is detachable from an assay part. This known device is provided with a test-ready indicator. The results of the assay are also not directly available to the user.

A problem is to provide reliable assay results. For example, in case a large number of persons is to be assayed by a large number of assay devices, it is important that a respective, large number of assay results is sufficiently reliable to determine who is likely to have certain conditions being tested for (such as certain diseases or physiological conditions).

SUMMARY OF THE INVENTION

The present invention aims to provide an improved assay device.

According to an embodiment, the assay device is characterized in that the device is provided with one or more assay context sensors configured to monitor one or more assay context factors.

In this way, assay results can be made more reliable in a relatively simple manner.

A basic idea behind the invention is to improve the accuracy/correctness of the measurement(s) by providing the assay device with one or more context sensors, for example at least a degradation monitor comprising a timer, or one or more different context sensors. For example, a context sensor can include a temperature sensor and/or a user condition sensor.

Besides, for example, in an embodiment, the device can be provided with one or more degradable assaying substances, the degradation of which is time-dependent, and a monitoring unit to monitor degradation of the one or more degradable assaying substances, wherein the monitoring unit is provided with a timer to time at least one degradation period of the one or more degradable substances.

Timing results, provided by the timer, can be used in various different ways to improve assaying results, as will be explained below. For example, a timed degradation of a substance can be used to determine whether or not a respective assay result is still sufficiently reliable. Also, the amount of degradation, detected via the timing of the degradation, can be used in calibrating or recalculating a respective assay result. Besides, the degradation monitor can be used to warn a user that the respective assay device is not suitable anymore to assay a sample, for example in the case that a certain maximum allowable degradation of a mentioned substance, or the reaching and/or passing of an expiration date, has been detected.

According to a further advantageous embodiment, the monitoring unit can be configured to use a detected degradation of the at least one degradable substance to correct an assay result obtained with the at least one degradable substance, particularly such that the corrected assay result is the result that would have been obtained if no degradation had taken place.

Degradation of the one or more degradable substances can take place in various ways. For example, degradation can start right after a device has been manufactured, and/or after the device has been sent to an individual for screening purposes. In that case, the device is provided with one or more degrading substances.

Also, in an embodiment, the degradation can start, or significantly increase, after activation of the device by the user.

Besides, in case the device comprises one or more degrading substances after its manufacture and/or after its sending or handing out, the degradation can change after the activation of the device. As an example, the activation can involve bringing the one or more degradable substances from a first state, wherein the substances are separated from air, to a second state wherein the substances are in contact with air to receive a sample.

Particularly, the one or more degradable substances are involved in the assaying of the one or more samples to be carried out by the device. For example, a degradable substance can include at least one of the following: a substance which is responsive to a specific analyte to be searched, one or more suitable enzymes, antibodies, binders or binding agents, a labeling substance, and/or micro-organisms and/or other suitable substances, as will be appreciated by the skilled person.

In an embodiment, the assay device can be provided with or connected to a memory unit, to store detected context data. For example, a memory unit wherein degradation information regarding degradation of the one or more degradable substances can be stored. Also, degradation information can at least comprise an expiration date, on which date the degrading of the one or more degradable substances has reached and/or passed a predetermined degradation threshold. The degradation information can also at least comprise a manufacturing date that relates to the manufacturing of the device and/or to sending the device to a desired user. The degradation information can comprise at least one predetermined degradation pattern of the substance degrading over time, or is configured to provide such a pattern.

According to an embodiment, there is provided a disposable assay device, configured to assay one or more samples and to provide at least one assay result relating to the assaying of the one or more samples, for example configured for transmitting assay data or information to a remote receiving system, preferably without disclosing the assay result to a user of the device, wherein the assay device is provided with at least one user condition sensor configured to detect at least one physical condition of a user of the device.

For example, in certain cases, the user condition sensor can determine or influence the accuracy of the measurement. As a non-limiting example, in the case that the assay device is configured to carry out a blood glucose test (for example the Fasting Plasma Glucose Test), it may be important that the person who's blood is to be tested is in a resting state. In that case, the user condition sensor can be configured to determine whether the user is in the desired resting state, before the device allows the test to be performed. The user condition sensor can be configured in various ways, and can comprise a personal activity sensor (for example having an acceleration sensor), a heart rate sensor, and/or one or more other types of user condition sensors.

Also, in an embodiment, the device can comprise a temperature sensor to measure the temperature of the environment of the device, wherein the device is configured to allow the assaying of a sample only after a temperature detected by the temperature sensor is within a predetermined temperature range, and/or to disallow the assaying of a sample in case the detected temperature is not in a predetermined temperature range. The temperature sensor can be used in combination with an above-mentioned user condition sensor, however, this is not essential since the temperature sensor can also be applied by itself in the assay device.

In an embodiment, there is provided a disposable assay device, configured to assay at least a first sample and to provide at least one assay result relating to the assaying of the sample, and configured for transmitting assay data or information to a remote receiving system, for example without disclosing the assay result to a user of the device, wherein the device comprises:

at least one testing unit to carry out the assaying of the sample, the testing unit being configured to provide a testing signal during at least part of a first time period, when the device has not received the first sample, and during at least part of a second time period when the device has received the first sample; and a memory unit;

the device being configured to store the testing signal, or information regarding the testing signal, both during the first and second time period, in the memory unit, and the device preferably being configured to store the testing signal in combination with a respective testing signal generation time.

Herein, a testing unit (for example, a sample application well) of the device can be part of an assay context sensor, or provide an assay context sensor. Thus, the testing unit not only carries out assaying of a sample but can also provide assay context information. For example, in this way, certain errors, for example due to contamination of the testing unit, can be detected in a simple manner after the test has been completed. For example, in this way, unexpected changes in the testing signal before a sample has been applied to the device, can be stored in the memory unit in order to be evaluated and detected after a subsequent processing of the results, for example in a remote processing facility. As an example, a testing signal can be stored continuously in the memory unit, or at predetermined time intervals, in a time period between an activation of the assay device and a time of application of a sample to the device. The testing signal may be stored as such. Also, testing signal-related information can be stored, for example a coded testing signal, a compressed testing signal and/or information or data derived from the testing signal.

Also, an embodiment provides an assay system comprising at least one device according to the invention, and at least one receiving system which is configured to receive assay data or information, the assay data or information relating to, being based on and/or comprising one or more assay results of the assay devices and/or comprising information that the assaying has failed.

In this way, the assaying of large groups of individuals can be performed in an economical, reliable manner.

Besides, an embodiment provides the use of at least one device according to the invention to assay at least one sample, for example a blood sample, of a user of the device.

Also, according to an embodiment there is provided an assay method, comprising:

providing at least one disposable assay device, the device being configured to assay one or more samples and to provide at least one assay result relating to the assaying of the one or more samples, preferably without disclosing the assay result to a user of the device, wherein the device is provided with one or more degradable assaying substances which take part in the assaying of the one or more samples, the degradation of the one or more degradable substances being time-dependent;

monitoring degradation of the one or more degradable assaying substances; and allowing use of the device only in case a monitored degradation of the one or more degradable assaying substances has not reached and/or passed a predetermined degradation threshold.

Besides, an embodiment provides an assay method comprising:

providing at least one disposable assay device, the device being configured to assay one or more samples and to provide at least one assay result relating to the assaying of the one or more samples, preferably without disclosing the assay result to a user of the device;

a user carrying the device; and detecting and/or monitoring at least one physical condition of the user carrying the device, before the device is used or can be used to assay one or more samples.

According to an embodiment, there is provided an assay method comprising:

providing at least one disposable assay device, configured to assay at least a first sample and to provide at least one assay result relating to the assaying of the sample, preferably without disclosing the assay result to a user of the device, wherein the device comprises at least one testing unit to carry out the assaying of the sample;

the generation of a testing signal by the testing unit during at least part of a first time period, when the device has not received the first sample, the resulting testing signal, or information relating to that signal, being stored, preferably, in combination with a respective time;

applying a sample to the device, so that the sample can be tested by the testing unit; and the generation of a testing signal by the testing unit during at least part of a second time period, when the device has received the first sample, the resulting testing signal, or information relating to that signal, also being stored, preferably, in combination with a respective time.

BRIEF DESCRIPTION OF THE DRAWINGS

Further advantageous embodiments of the invention are described in the dependent claims. These and other aspects of the invention will be apparent from and elucidated with reference to the embodiments described hereafter.

DETAILED DESCRIPTION

In the present application, similar or corresponding features are indicated by similar or corresponding reference signs.

There are 20.8 million people in the United States, or 7% of the population, who have diabetes. While an estimated 14.6 million have been diagnosed with diabetes, 6.2 million people (or nearly one-third) are unaware that they have the disease.

Today, in order to determine whether or not a person has pre-diabetes or diabetes, health care providers conduct a Fasting Plasma Glucose Test (FPG) or an Oral Glucose Tolerance Test (OGTT). Either test can be used to diagnose pre-diabetes or diabetes.

Instead of the person having to go to the care provider, the person may perform the test at home. For example, the person may put a blood sample on a device that is capable of conducting a glucose test.

For a number of medical measurement protocols, it is necessary to perform a sequence of measurements instead of only one measurement. While it is known in the art to include multiple application wells on an assay part of an assay device, the existing technology is not suitable for measurement protocols that require significant amounts of time to pass between each measurement. For example, to have a better-quality assessment it can be beneficial to repeat the measurement for 3 consecutive days. In a known device (see EP972196B1), the assay part can only be detached at the end of this period. During this period there is the risk of bio-contamination, as the first application well contains biomaterial after the first assaying step. For example, this risk can be avoided by independently removable application wells w, as can be seen from embodiments shown in FIGS. 1-2. Besides, assay results provided by a known device can be unreliable for various reasons; also, various errors in the assay results can be hard to detect after the assaying has been completed.

Figure 1:
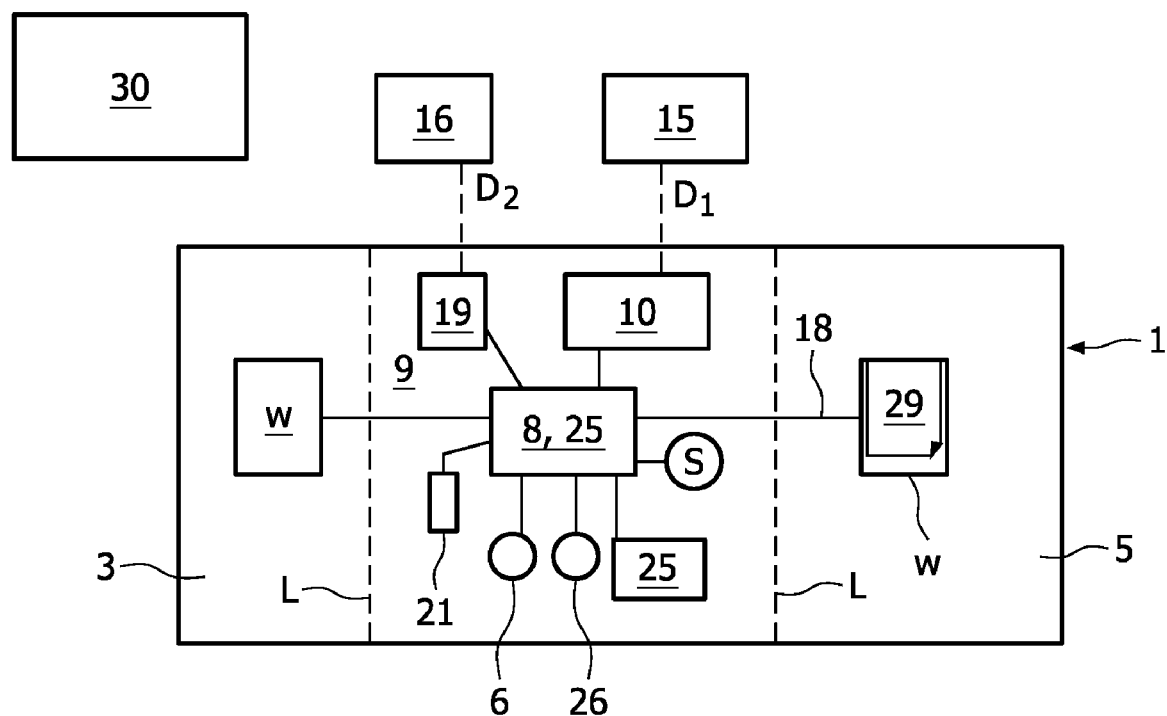
FIG. 1 schematically shows a first embodiment of an assay device according to the invention.

FIG. 1 schematically shows an embodiment of a disposable assay device 1. The device shown in FIG. 1 comprises two sample application areas w. Alternatively, for example the device 1 can comprise one sample application area, or more than two sample application areas.

For example, the device 1 comprises a carrier or substrate having two first carrier parts 3, 5 with respective sample receiving areas w (for example application wells w) for receiving samples to be tested, and having a second carrier part 9 comprising a memory device 10 configured to store assay results relating to tested samples. The carrier 3, 5, 9 can be made of various materials, for example a suitable paper or paper-like material, plastic and/or other materials. Also, the first carrier parts 3, 5 may be independently removable (i.e. independent with respect to each other) from the second carrier part 9, to independently remove the respective application wells w from the second carrier part 9.

Advantageously, the assay device 1 is configured for transmitting assay data or information to a remote receiving system 30. For example, the device 1 can be configured to store the assay results without disclosing the results to a user of the device 1 (herein, a user of the device 1 is generally a person who, during use of the device 1 to assay one or more samples, applies an above-mentioned sample to an application well w of the device 1). The assay device 1 can be configured to assay one or more samples and to provide at least one assay result based on the assaying of the one or more samples.

For example, the device 1 can be used to assay individual users of an assay system, for screening purposes. Individuals to be tested by the device 1 can be human individuals. However, alternatively, the devices can be configured to assay animals or vegetation.

Besides, assays to be conducted with the device 1 may involve screening of certain other areas or locations, for example screening of environments (air, water, soil, etc.) for contamination, certain substances and/or organisms.

The assay device 1 can be configured to detect various types of analytes. For example, analytes to be determined may include glucose, pregnancy related analytes, cholesterol, drugs, biotoxins, diseases, cardiac markers, chemicals, hormones, proteins, and/or other analytes. Other analytes may include certain substances, toxic matter, environmental contamination and/or different analytes.

The assay device 1 can be configured to assay various types of samples, for example samples of blood, body fluid, saliva, urine, plasma, serum and/or other sample types, as will be clear to the skilled person. Also, the different application wells w can be used to receive different samples, for example in a predetermined sequence and/or after predetermined time periods. Alternatively, different application wells w of the device can be used to receive parts of the same sample, if desired.

Besides, advantageously, the assay device 1 is portable, lightweight, and compact, for example having a relatively flat credit card format, or sheet-like configuration. For example, the assay device 1 can be configured so as to be sent to users in a simple envelope or package, or by or as part of a letter, by regular mail.

The assay device 1 can be configured in various ways to conduct an assay on a sample, as will be clear to the skilled person. For example, the assay device 1 can be provided with one or more substances, for example one or more suitable enzymes, antibodies, binders or binding agents, a labeling substance, and/or microorganisms, which can be responsive to a specific analyte to be searched for. In particular, one or more of these substances can be degradable over time, for example in case a substance is self-degrading, or degradable by contact with an environment of the device and/or with air. An analyte and/or analyte-dependent modifications can be detected, for example, optically, electrochemically, by electrical resistance measurement, and/or in a different way, by the assay device 1. Testing of the analyte can be conducted, for example, at the respective sample-receiving areas (or sample wells) w, or at other locations of the assay device. Such sample-receiving areas w can also be called testing units, or can be part of testing units, wherein a testing unit w can be configured to provide a testing signal. In a further embodiment, for example, a testing unit w can provide a testing signal during at least part of a first time period, when the testing unit w has not received a sample, and during at least part of a second time period which starts substantially from the moment that the testing unit w has received a sample. This will be explained below with reference to FIG. 3. Alternatively, a testing unit w can be configured to provide a testing signal only after having received a sample. For example, a testing unit or sample-receiving well w of the device 1 can be provided with at least one degradable substance which is responsive to a specific analyte to be searched for, in which case the mentioned testing signal can be dependent on the amount and/or condition of the at least one degradable substance.

In the present embodiment, the first and/or second carrier parts comprise microelectronics configured to assay the samples, provide respective test results and store the results in the memory 10. To this aim, for example, the microelectronics can cooperate with and/or be electrically connected to the mentioned sample-receiving wells w in a suitable manner, to carry out the assaying of the samples, as will be clear to the skilled person. Preferably, the second carrier part 9 is provided with a major part (for example more than 50% and particularly at least 90%) of the microelectronics, for example with substantially all of the microelectronics. The testing can be controlled, for example, by a suitable controller 8 of the device. In a more detailed analysis of the architecture of the device, it can comprise a controller 8, connected to an A/D convertor through a digital connect, that is connected through one or more analog connects 18 to application wells w. Preferably, the A/D convertor is provided on the second carrier part 9, for example integrated with the controller 8, for cost saving and to reuse the A/D convertor for multiple application wells, and recycle it.

A mentioned test result which is stored in the memory device 10 can include various types of results, for example a numerical value, a plurality or an array of numerical values, or a test result graph (see FIG. 3), or a true-false value (or "positive-negative", 0-1, True-False) relating to a successfully conducted sample assaying. On the other hand, in case an assay is inconclusive or fails—such as due to a device failure, a test result can be "assay inconclusive", "assay failed", "device failure" or a similar result.

In a further embodiment, the carrier can be provided with a low-cost write-once display, configured to subsequently provide operating steps to be taken by a user of the device 1, during use. Besides, in an embodiment, the device can be provided with a user interface, preferably comprising multiple-choice buttons. Further, the carrier can advantageously be provided with a user guide configured to guide a user in the applying of samples to the first carrier parts, wherein the user guide preferably is arranged to indicate a predetermined sequence of use of the first carrier parts. For example, the user guide can be provided in printing, or via audiovisual means such as an optional display 38 and/or loudspeaker 35 of the device (see FIG. 2) that is/are controllable by the controller 8.

Each sample-receiving area w can be provided to receive a respective sample. Detection areas can be provided for testing the samples that have been received at the receiving area 3 during use. The first carrier parts 3, 5 and/or second carrier part 9 can be provided with such detection areas. For example, an assay device 1 can comprise a plurality of sample-receiving areas w and one respective detection area, the detection area for example being located on the second carrier part 9. Alternatively, on/in the assay device 1, one sample-receiving area w can be associated with several respective detection areas, for example to assay one sample, received on that receiving area w, for different analytes. Besides, an assay device 1 can comprise several sample receiving areas and several respective detection areas, to test several samples. For example, sample-receiving areas w and detection areas can be integrated with each other, or be spaced-apart from each other. In the latter case, for example, sample conductors can be provided, for example capillary channels, to conduct one or more samples, or parts thereof, from one or more receiving areas w to one or more detection areas, for example using capillary action, gravity, or in a different manner. Besides, for example, the assay device can be manipulated, for example via folding or bending, to bring a sample-receiving area into contact with a detection area. Each assay device 1 can also be configured in a different manner.

In an embodiment, as an example, the two first carrier parts 3, 5 can be configured to carry out the same assay test, particularly to test a sample for the same analyte. Alternatively, the first carrier parts 3, 5 can be configured to carry out different assay tests, particularly to test samples for different analytes.

Also, each of the assay devices 1 can be configured to provide at least one assay result based on the assaying of the one or more samples. The mentioned controller 8 of the device 1, for example a microelectronic processor or CPU (Central Processing Unit) 8, can be configured to control and process the assaying of samples, which are received at the receiving areas w. In this case, the memory 10 is controllable by the controller or processor 8 to store the test results. As an example, the controller 8 and memory 10 can be integrated with each other, or can be separate components. Also, for example, the embodiment of FIG. 1 can comprise a so-called lab-on-a-chip system, and, for example, the controller 8 can comprise a lab-on-chip processor which can at least partly include a mentioned detection area.

Besides, the assay device can be provided with a test result transmitter 19 configured to transmit a test result to an external test result receiver 16. Herein, for example, data transmission between transmitter 19 and receiver 16 (which data transmission is schematically indicated by a dashed line D2) can take place via suitable wiring and/or wirelessly, for example using electric, electromagnetic and/or optical signals, a network interface or digital output, or differently.

Advantageously, the memory 10 can be read by an external memory-reading device 15 for obtaining the test result from the assay device 1. For example, data transmission between the memory 10 and reading device 15 (schematically indicated by a dashed line D1) can take place via suitable wiring and/or wirelessly, for example using electric, electromagnetic and/or optical signals, a mentioned test result transmitter 19, or differently.

A mentioned external test result receiver 16 and memory reader 15 can be configured in various ways, and can include a dedicated docking station for docking the assay device 1C, a computer, a personal digital assistant (PDA), a mobile phone, and/or can be part of a remote receiving system 30 (schematically depicted in FIG. 1) and/or can be configured differently. For example, in an embodiment, the external test result receiver 16 and memory reader 15 can be integrated with each other.

Components of the assay device 1 can be powered in various ways, for example by a solar cell, a battery, by charging, by inductance, by self-powering or capillary action, by a storage capacitor, by power storage via motion and/or a winding mechanism, or differently.

In the present embodiment, the test result storage part 9 of the device 1, for example comprising the memory 10, and preferably comprising the processor 8 and transmitter 19, might be separable from each respective sample receiving area w. Also, as an option, an assay device 1 can be provided with a test ready indicator 6, for example a LED (light emitting diode) or speaker or the like, to indicate when an assay of a sample is finished. In the present embodiment (see FIG. 1), the second carrier part 9 comprises the test ready indicator 6.

For example, the assay device 1 provides assay data or information, the assay data or information relating to, being based on and/or comprising one or more assay results of the assays carried out by the device 1. Advantageously, the device 1 is configured to keep the test result secret to the user of the device, similar to devices known from WO 95/33996. For example, the device 1 can be configured to provide the user with a code, which is to be sent to a central receiving system 30.

As an example, the receiving system 30 can be configured to receive assay data or information (which can comprise the afore-mentioned code), the assay data or information relating to, being based on and/or comprising one or more assay results of the assay devices 1 and/or comprising information that the assaying has failed. Transmission of the mentioned assay data or information (or code) to the central receiving system can comprise, for example, electronic transmission, transmission via a computer and/or telephone network, transmission via a communication connection between a user communication terminal and a communication terminal of the receiving system, transmission via regular mail and or transmission via locally available test result collection facilities, depending for example on the configuration of the respective assay device 1. Also, for example, the user can send (i.e. transmit) the whole assay device 1, or preferably only the memory comprising part 9 thereof, containing assay data or information, to a remote receiving system 30.

The skilled person will appreciate that the receiving system 30 can be configured in various ways. For example, the receiving system 30 can be provided with a computerized call receiving system, and/or voice response system, configured to receive calls from the users, for example receive the assay data from the users, communicate with users and/or return test result-related information back to the users. Besides, in an embodiment, the receiving system 30 can be configured to cooperate with, or be provided with, an assay device distribution system, to distribute one or more assay devices 1 to a user, for example depending on received assay data or information from an assay device 1 used earlier by that user.

Also, for example, the receiving system 30 can at least be configured to determine, using received assay data or information, whether a respective assay result from an assay device 1 is a negative or positive assay result, and/or whether the result is inconclusive, and/or whether the assaying has failed and, optionally, a/the reason(s) why the assaying has failed. Then, in a further elaboration, a distribution system/receiving system 30 can be configured to distribute at least one further assay device to a user U of a prior assay device in case the receiving system 30 has determined that a respective assay result from the prior assay device 1 is a positive assay result, and/or an inconclusive result. For example, a more accurate assay device can be sent to the user, who provided a positive or inconclusive test result using a prior assay device, to confirm the positive test result, or to redo the assay, respectively, with higher accuracy.

Besides, in an embodiment, the receiving system 30 can at least be configured to determine, using received assay data or information, at least one type of deviation concerning received assay data or information with respect to threshold data or information, estimated data or information, and/or expected data or information. Also, in an embodiment, the receiving system 30 can be configured to receive at least removed parts 3, 5 of used assay devices 1, and to perform at least one of the following: detect damage and/or malfunction of received assay devices or of parts thereof, read data or information from received assay devices or parts thereof, recycle received assay devices 1 or parts thereof. For example, to detect damage and/or malfunction of received assay devices or of parts thereof, the receiving system can be provided with suitable sensors and/or detectors, as will be clear to the skilled person. The receiving system 30 can be configured, for example, to detect a color and/or optically detectable test result indicators of a received assay device or part thereof.

In the embodiment of FIG. 1, the device 1 is provided with a central second part 9, which is bounded by first parts 3, 5 extending on opposite sides of the second part 9. Both first carrier parts 3, 5 can be detachably coupled to the second carrier part 9. Such detachable coupling can be configured in various ways. For example, the carrier can be provided with weakening lines or perforation lines L, extending between the first and second carrier parts 3, 5, 9 for independently removing the first carrier parts from the second carrier part. The weakening lines or perforation lines L are such that a user can tear off or break off each first carrier part 3, 5 from the second memory-comprising part 9 via those lines.

Preferably, the assay device 1 is configured to detect the removal of a first carrier part 3, 5 from the second part 9. Also, preferably, the device 1 is configured to record a time of the removal of the first assay part in the memory device 10. Such detection and/or time recording can be carried out, for example, by the controller 8. Detection of removal of a first carrier part 3, 5 can be achieved using, for example, tear off detectors, for example respective electrically conducting detection lines or loops that are coupled to the controller 8, and that are interrupted or broken when a respective first carrier part 3, 5 is removed from the second part 9.

In a further embodiment, the device 1 can be configured to record each assay result, in combination with identification information from a respective first carrier part 3, 5 leading to that assay result (i.e., the first carrier part 3, 5 which received a respective sample), in the memory device 10. Also, the device 1 can be configured to record each assay result, in combination with time information concerning a respective assay leading to that assay result, in the memory device 10. Other types of information can also be stored in the memory device 10, for example assay context information, for example information provided by one or more assay context sensors 8, 20, 21, 25 that relates to one ore more monitored assay context factors. For example, the assay device 1 can be configured to monitor assay context before, during and/or after assaying a mentioned sample, and preferably to store the results of such monitoring in the memory device 10. For example, the assay device 1 can be provided with one or more assay context sensors 20, 21, 25 to detect temperature, humidity, contamination and/or other assay context factors. As an example, one or more such sensors can be integrated in the controller 8, or connected thereto in a suitable manner. An advantageous embodiment of a mentioned context sensor is a degradation monitor, which is described in more detail below.

During use of the embodiment of FIG. 1, the device 1 can be provided to a user, for example by postal delivery, by handing-out or in a different manner. The user can use the device 1 (for example at home or in another suitable location) in an assay method, by applying one or more samples to the application wells w of the first carrier parts 3, 5 of the device 1 to test the samples for the presence of one or more analytes. Test results, relating to the testing of the samples, are stored in the memory 10 of the device, without displaying or otherwise disclosing the results to the user. Preferably, the user removes each first carrier part 3, 5 from a remaining device part after having used that first carrier part. Thus, cross-contamination can be avoided, and all assay results can be stored in the same memory 10. After both first carrier parts 3, 5 have been used and removed, the remaining second part 9 can be returned to a central receiving/processing facility, to deliver the memory 10 and its results. Alternatively, such results can be sent using suitable communication means, as mentioned above. Thus, a sequence of measurements can be performed, instead of only one measurement, in a safe, efficient and accurate manner. For example, a better quality assessment can be obtained when the measurement is repeated after a predetermined time period of 1 day (circa 24 h).

For example, the first carrier parts 3, 5 of the device can be used sequentially with a predetermined intermediate time period. The device 1 can be configured to indicate this time period, for example via a suitable display 38. Also, the device 1 can be provided with a timer, for timing the lapsing of the predetermined time period. The device can be configured to indicate to the user when the predetermined time period has lapsed, to encourage the user to use the next first carrier part for a subsequent assay.

The embodiment of FIG. 1 provides the advantage that the user can use any application wells w first, as they can be independently detached. If the different assay parts contain different tests, this allows freedom in the order in which tests are taken. Besides, all first carrier parts can be the same in set-up, and wiring of electronic parts can be relatively straightforward. This simplifies the card design and lowers material costs.

Figure 2:
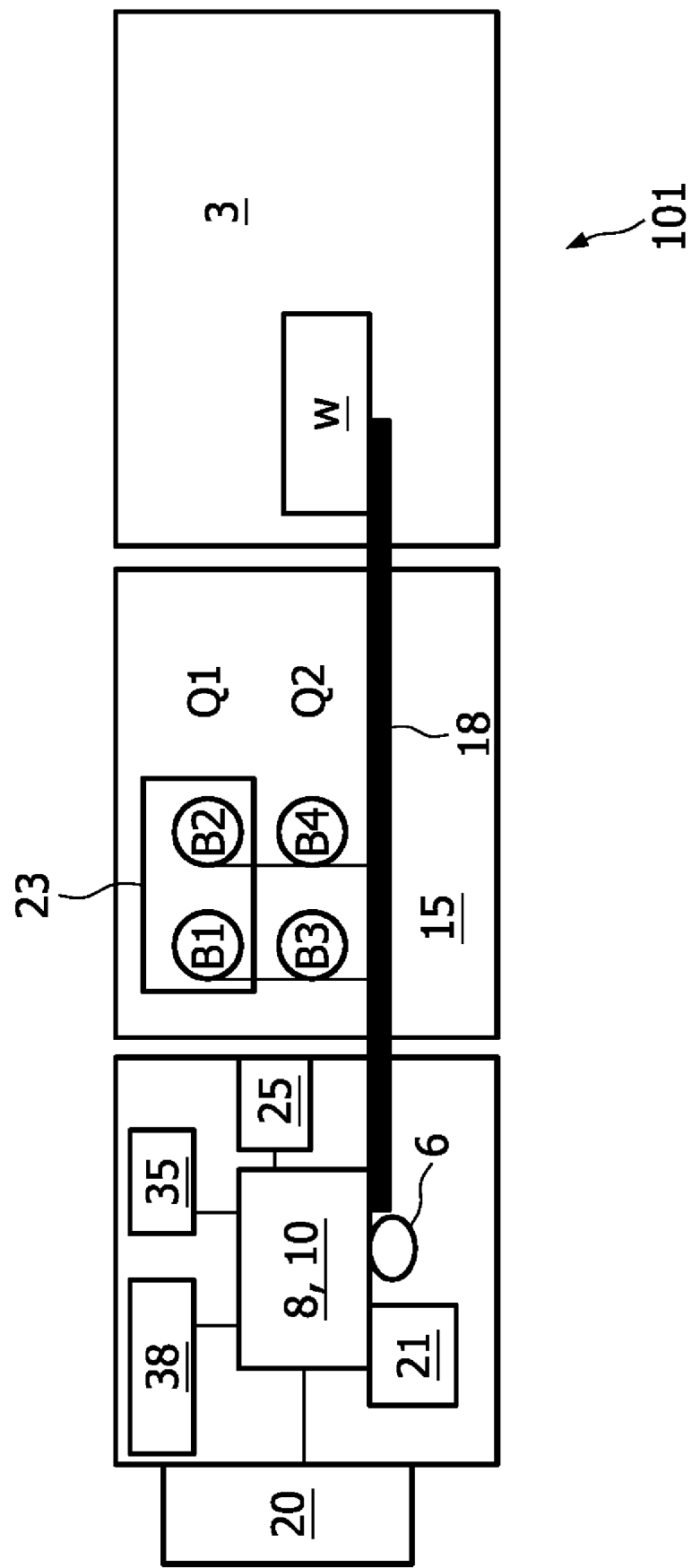
FIG. 2 shows an alternative embodiment of an assay device.

FIG. 2 shows another embodiment of an assay device 101, being provided with a user interface, for example multiple-choice buttons B1-B4, a display 38 and a speaker 35. The multiple-choice buttons B1-B4 can be associated with respective questions Q1-Q2, for example printed next to the buttons and/or on the buttons. The device can be provided with a specific, dedicated carrier part 15 comprising the questions Q and/or buttons B, which dedicated carrier part 15 can be removably connected to the second carrier part 9 which has been provided with a controller 8 and memory 10. Alternatively, the dedicated carrier part 15 and second part 9 may be integrated with each other. The embodiment of FIG. 2 is provided with only one first carrier part 3 having a single sample application well w. In the present embodiment, the first carrier part 3 is removably connected to the dedicated user interface carrier part 15. For example, the second carrier part 9 can be provided with a user interaction means 6, for example a test ready indicator. Thus, detaching the first carrier part 3 results in a minimal loss of functionality for the device 101. As the first carrier part 3 is disposed (it is potentially contaminated), the embodiment of FIG. 2 provides a design where functionality is placed on the recording part when possible. Specifically, any user interaction means, like the test-ready indicator 6 (or the multiple-choice buttons), are placed on the second carrier part 9. In this way, these user interaction means can be used to continue an interaction with the user, even after the detach operation. For example, the second carrier part 9 needs to be returned to a central processing facility, and the user can be reminded of this aspect by blinking of the test-ready indicator 6 at intervals, thus focusing the attention of the user on the "to-be-sent" in device 101.

Device activation can be achieved in various ways, for example by a user pressing a start button S (see FIG. 1) or other buttons B (see FIG. 2), by activation of a sample application well (or testing unit) w and/or in a different manner. As an example, the device 1 can be configured to be in a non-operating state (for example an idle mode), in which case an application well w is not available to receive the sample, and in an operating state when the testing unit w is available to receive the sample. A simple example is an application well w, being provided with a removable cover or tear-off cover 29 (see FIG. 1), wherein the testing unit w can be brought into the operating state by removing the cover 29 from the well w. In case a plurality of testing units or application wells w is provided, various respective non-operating states and operating states can be available (one for each application well w).

From the above it follows, as shown in FIGS. 1 and 2, that, advantageously, the device 1, 101 can be provided with one or more context sensors, for example a user condition sensor 20, a temperature sensor 21 and/or a timer 25. Each of these sensors can be integrated in a mentioned controller 8 or can be provided separately on a carrier part 3, 5, 9. Alternatively, a sensor 20, 21, 25 can be connected to the device controller 9 via suitable communication means, for example suitable wiring, a wireless communication link or other connection means, to transmit sensor data to the controller 8.

As is mentioned above, the device 1 can be provided with one or more degradable (for example degrading) assaying substances. As an example, a device application well or testing unit w can be provided with one or more degradable substances. The degradation of the substances can be time-dependent. For example, after a certain expiration date (such as, from a certain device manufacturing date), the one or more degradable substances are not suitable anymore for use in the assaying of samples. The degradation can involve chemically induced degradation, thermally induced degradation, radiation induced degradation, physically induced degradation and/or any other type of degradation of the substance(s).

Preferably, the device 1 is provided with a monitoring unit to monitor degradation of the one or more degradable assaying substances. In the present embodiment, the monitoring unit can simply be provided by the controller 8. Alternatively, a dedicated monitoring unit can be provided, which can be connected to the device controller 8 in a suitable manner for data exchange.

In an embodiment, the degradation monitoring unit (controller) 8 is provided with the timer 25 to time at least one degradation period of the one or more degradable substances. For example, the timer 25 can be configured to count time in various time units, for example seconds or parts thereof, minutes, hours, days, months and/or years. The timer 25 can be configured to count time up from zero, from a device manufacturing time, from a device shipment time, or from another starting point. The timer 25 can also be configured to count down time, for example from a predetermined device expiration time to zero. Also, as an option, the timer 25 can be provided with a calendar and/or can be calibrated to provide the actual time/real time. In this way, the time-dependent degradation can be monitored in various ways, and certain actions can be taken by device 1 depending on the outcome of the monitoring or degradation timing.

For example, in a further embodiment, the device comprises at least one testing unit w (for example comprising an application well w) to carry out the assaying of a sample. In an embodiment, the testing unit w can be configured to provide a testing signal (for example an electric signal, electronic, optical or other suitable signal, an analogue or digital signal) during at least part of a first time period, when the device 1 has not received the first sample, and during at least part of a second time period when the device has received the first sample. Thus, the testing unit w can provide an assay context sensor as such, or be part of an assay context sensor system.

As an example, the testing unit can be configured such that the testing signal is being generated continuously, for example during the lifetime of the device 1, or at predetermined time intervals. Also, as an example, to reduce power consumption, the generation or transmission of the testing signal can start automatically from the moment the device is being activated.

Advantageously, the device 1 (for example the controller 8 thereof) can be configured to store the testing signal, or information regarding the testing signal, both during the first and second time period, in the memory unit 10. As is mentioned above, a testing signal may be stored as such, or testing signal related information can be stored, for example a coded testing signal, a compressed testing signal and/or information or data derived from the testing signal. Preferably, the device 1 is configured to store the testing signal in combination with a respective testing signal generation time (for example approximately the time when the signal was generated by the unit w and/or received by the processor 8).

For example, the device 1 can be configured to store the mentioned testing signal, or information regarding the testing signal, during at least part of a time period when the device 1 is in the non-operating state.

For example, during use (see FIG. 3), there can be provided an assaying method, wherein a testing signal is being generated by device 1 during at least part of a first time period, when a testing unit w has not yet received a sample. The resulting testing signal, or information relating to that signal, is stored, preferably in combination with a respective time, in the memory 10. The first time period can run from a time T1 at which the device 1 is being activated (for example by tearing off a mentioned cover 29 from the application well w). Alternatively, the first time period may run from an earlier point in time, for example from a time when the device 1 has been sent to a user, or a time of manufacture.

Next, at a time T3, a sample is applied to testing unit w in order to be tested thereby, wherein the testing signal is still being generated by the testing unit w, at least until the test is ready. The resulting testing signal, or information relating to that signal, is being stored, preferably as a function of the respective time (for example in a data list or graph). Herein, for example, a mentioned second time period can run from the sample application time T3 to a test-ready-time T4 (as an example, the controller 8 and/or a testing unit w can be configured to automatically determine when the test is ready, and to determine a respective test-ready-time T4 in cooperation with the timer 25).

Figure 3:
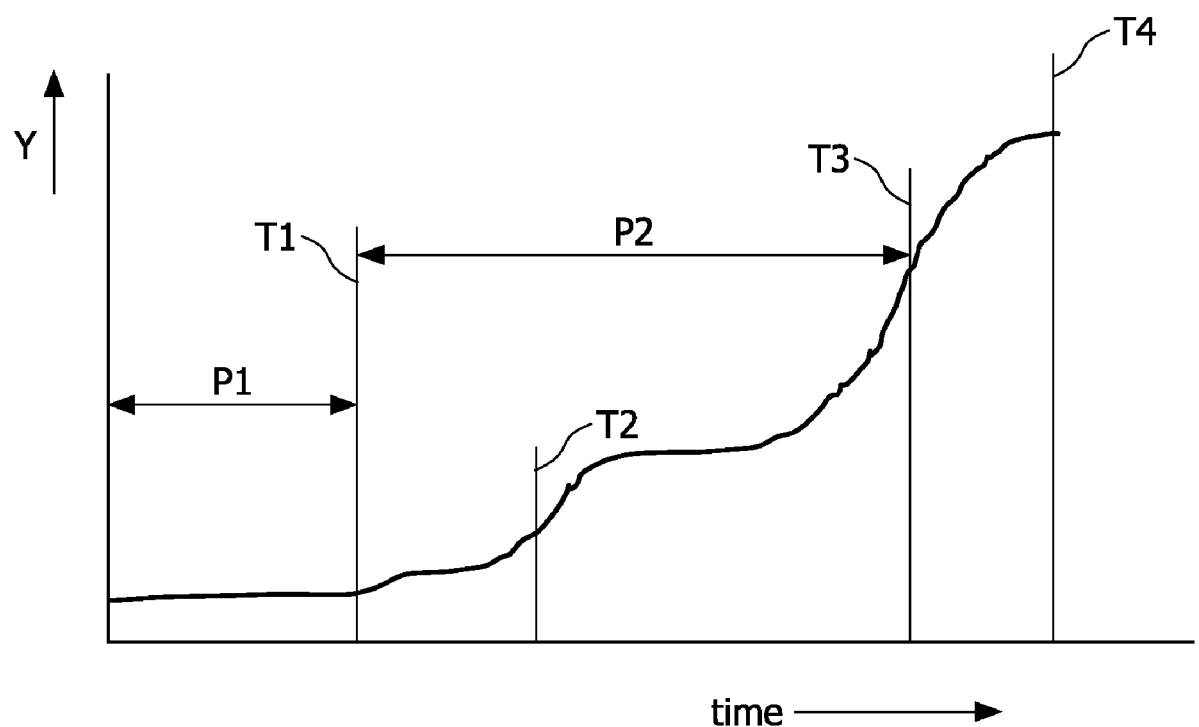
FIG. 3 shows a graph indicating a measured assay result versus time.

FIG. 3 schematically depicts a result of this method, the result comprising a testing signal Y as a function of the time (t). For example, the result shown can be stored in the memory 10, for example in combination with mentioned time periods, a device activation time T1, sample application time T3 and/or test-ready time T4. The result can be transmitted in a suitable manner to a remote central processing facility 30.

In the depicted test result, from a time T2, an unexpected rise of the testing signal Y is present, after activation of the device 1 (time T1) but before the sample is being applied (time T3). For example, the rise might be caused by contamination of a sample receiving area w, and/or by degradation of one or more testing substances, which degradation is not related to the sample.

For example, if an application well or testing unit w can measure continuously, any changes in read-out after activation of the testing unit but before completion of the test, can be stored as a time-sequence (as in FIG. 3). By analyzing this sequence it can be identified if the application well was contaminated.

Thus, by determining and storing the testing signal, or related information, as a function of time, potential assaying faults can be detected in a simple manner. A remote receiving system 30 can be configured to reject test results in case received assay data comprises such unexpected assaying deviations. Also, the device 1 as such (for example the controller 8) can be arranged to reject an assay result on similar grounds.

The application of a timer 25 can also be advantageous to monitor for potential assaying problems in case the device 1 is provided with one or more degradable substances (as mentioned above). This will be explained below, referring to FIG. 4.

For example, the device 1 can be configured to be in a non-operating state, in which case the one or more degradable substances are not available to receive a sample, and in an operating state when the one or more degradable substances are available to receive a sample. The monitoring unit 8 and timer 25 of the device can then be configured to cooperate to measure at least a first degradation period P1 (which is also indicated in FIG. 3 by a double-headed arrow) during which the device 1 is in the non-operating state.

Also, the monitoring unit 8 and timer 25 can be configured to cooperate to measure at least a second degradation period P2, which period is the time between activation of the device, on the one hand, (for example a time T1) and the receiving of a sample by the one or more degradable substances on the other hand (for example a time T3). As an example, degradation of a substance might increase after activation of the device 1 (for example, in case the activation involves opening an application well w, so that a degradable substance is subjected to a substance degrading environment). An example of a second degradation period P2 is indicated in FIG. 3 by means of another double-headed arrow.

In case a substance of the device 1 degrades both during the mentioned first degradation period and the second degradation period, advantageously, the degradation monitor 8 can be configured to take into account both the measured first degradation period and second degradation period to determine or estimate an overall degradation of the degradable substance. Also, the degradation monitor 8 can be configured to take into account certain predetermined degradation rates of each degradable substance (which rates may be stored in the memory 10), for example a first degradation rate of the substance degrading during a first degradation period and a second degradation rate of the substance degrading during a second degradation period. In each case, a mentioned degradation rate can have been analytically determined beforehand by computer simulations, empirically and/or in other suitable ways, as will be appreciated by the skilled person.

In an embodiment (see FIG. 1 or 2), the monitoring unit 8 can be provided with or connected to a memory unit 10, wherein degradation information regarding degradation of the one or more degradable substances is stored in the memory unit 10. For example, the stored degradation information can at least comprise an expiration time or date, at which time or date the degradation of the one or more degradable substances has reached and/or passed a predetermined degradation threshold. For example, maximum degradation periods, or expiration periods, can be stored in the memory 10, which are to be used by the degradation monitor 8 and timer 25 to determine whether or not the device 1 still can be used to reliably assay a sample. Besides, the degradation information can at least comprise a manufacturing date that relates to the manufacturing of the device 1 and/or to the sending of the device 1 to a desired user.

A mentioned degradation threshold can depend on the type of degradation. For example, the amount of a degrading substance may decrease over time; in that case, a mentioned degradation threshold can be a predetermined percentage (%) of the amount of the degrading substance still present in the device 1 with respect to an initial amount of the substance (for example, the amount just after the device 1 was manufactured), below which percentage the device 1 cannot carry out a reliable measurement anymore. Besides, as an example, the degrading of a substance can mean that a substance's reactivity or a sensitivity to an analyte decreases over time, in which case the degradation threshold can be related to a minimum desired reactivity or a sensitivity of the substance.

In an embodiment, the device 1 (or its memory) can also be provided with a first expiration time ET1 (which can comprise a date) relating to a maximum allowable non-operational period of the device 1. Besides, the device 1 (or its memory) can be provided with a second expiration time ET2, which starts from a moment of activation of the device 1, and which can relate to a maximum allowable operational state of the device during which a sample can be applied to the device 1 in order to be tested by the device 1 in a sufficiently reliable manner. Both the first and second expiration times ET1, ET2 can be fixed values. However, advantageously, the device 1 is configured to automatically adjust the expiration times ET1, ET2 in case of varying circumstances, for example in case of detected temperature changes (detected by temperature sensor 21) that can influence substance degradation. Also, the length of the second expiration time ET2 can be dependent on the length of a previous first degradation period P1 (for example: the longer a first degradation period P1, the shorter a second expiration time ET2).

In a further embodiment, the device 1 can be provided with degradation information comprising at least one predetermined degradation pattern of the substance degrading over time, or is configured to provide such a pattern. For example, the stored degradation pattern can be an empirically determined pattern, a calculated or simulated pattern. Also, the degradation pattern can be provided by a theoretically derived mathematical or statistical formula stored in the device 1. Such a stored degradation pattern can be used, for example, to recalibrate the device 1 prior to assaying a sample, or correct an assay result. Also, in an embodiment, the monitoring unit 8 can be configured to use a detected degradation of the at least one degradable substance to correct an assay result obtained with the at least one degradable substance, particularly such that the corrected assay result is the result that would have been obtained if no degradation had taken place.

Preferably, the monitoring unit 8 is configured to disallow use of the device in case a monitored degradation of the one or more degradable assaying substances has reached and/or passed a predetermined degradation threshold. For example, the monitoring unit 8 can be configured to block the use of a sample receiving area w.

Also, the monitoring unit 8 can be provided with or connected to an indicator, for example a display 38 and/or a speaker 35 (see FIG. 2), to indicate a time remaining for the user to use the device to assay a sample, wherein the remaining time depends on degradation of the one or more degradable assaying substances.

Besides, as follows from the above, the device 1 can be configured to detect activation of the device 1 and to detect the application of a sample to the device 1, wherein the device 1 is configured to store a time and/or date of the activation of the device, as well as a time and/or date when the device receives the sample, the mentioned times and/or dates being provided by the timer 25.

An embodiment of an assay method comprises providing an assay device 1, and monitoring degradation of one or more degradable assaying substances of the device. Herein, use of the device can be allowed only if a monitored degradation of the one or more degradable assaying substances has not reached and/or passed a predetermined degradation threshold.

Figure 4:
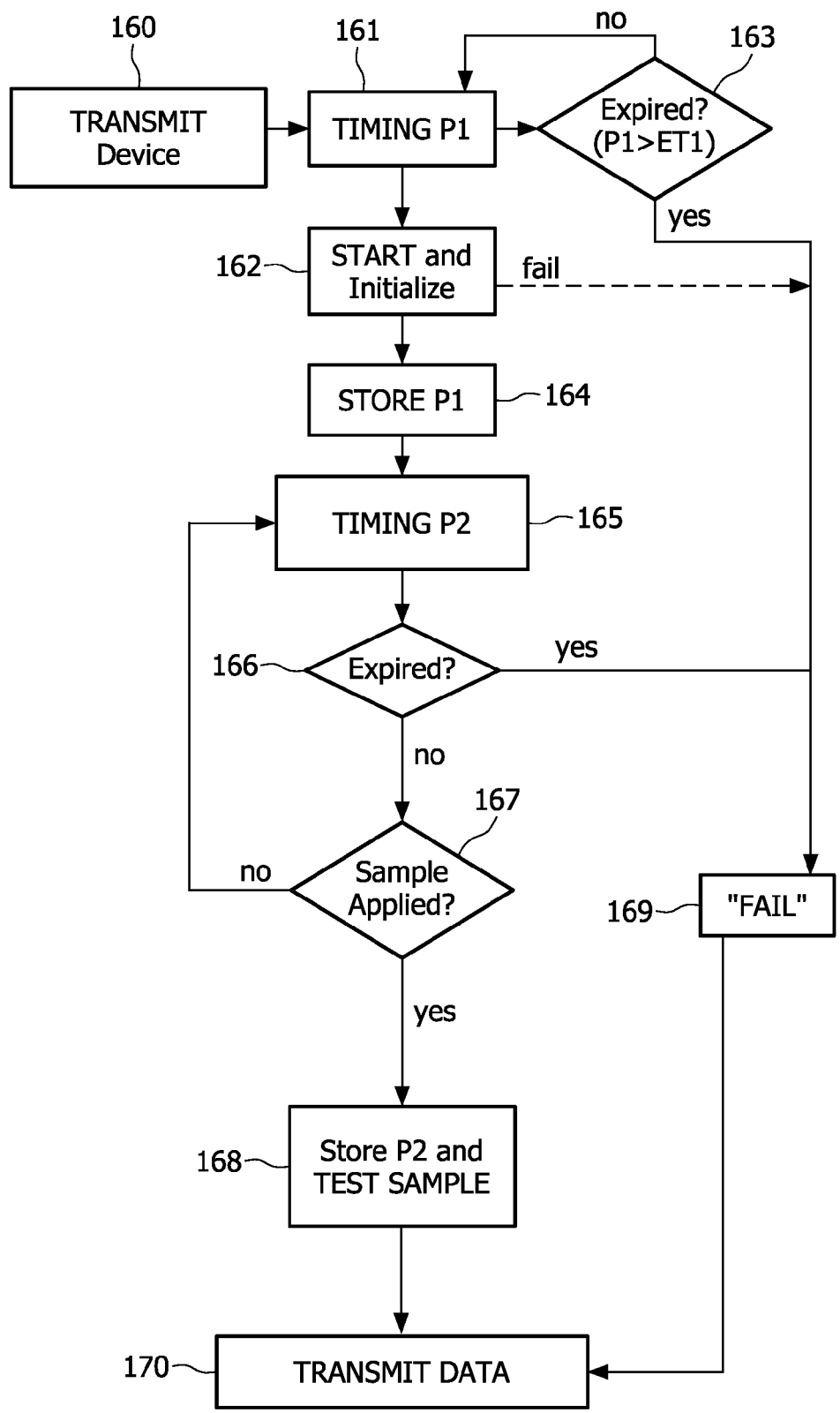
FIG. 4 shows a flow chart of an assay method.

FIG. 4 shows a flow chart of an assay method, using for example an embodiment of an assay device shown in FIG. 1 or 2 and certain logic steps that can be carried out by the device 1. The assay device 1 is first distributed to a user to be screened (step 160: transmit device). A first degradation period P1, relating to time-dependent degradation of at least one degrading assaying substance of the device 1, is subsequently measured by the device 1 (step 161). During this period, the device 1 is in an idle mode of operation. During the idle mode, the device controller 8 regularly checks (step 163) whether the first degradation period passes a predetermined respective first expiration time ET1 (which can be stored in the memory 10 of the device 1). In the case that the first expiration time ET1 is passed, use of the device 1 is automatically blocked via a "Fail" step (169). A resulting "assay failed" result, preferably combined with the reason of failure (for example "device passed first expiration time") can then be transmitted (step 170) to the remote processing facility 30. Also, a fail-message can be indicated to a user, to warn the user that the device is not suitable to be used anymore.

For example, the device 1 can carry out a logic step: "IF a timed first degradation period P1>first expiration time ET1 of application well chemicals, THEN warn user that the device is no longer usable".

On the other hand, in the case that the first expiration time has not passed, the user can bring the device 1 into an operating state (for example by pressing a start button, or by tearing off a mentioned cover 29). Optionally, in this start-and-initialization step 162, the device 1 can perform a self-check and/or can carry out a certain interactive user guidance (for example via multiple-choice buttons B). In the case that the device initialization fails, for example due to device failure or due to a result of the user interaction, preferably, the device 1 automatically performs a "fail"-step (169).

On the other hand, when device initialization succeeds, the device 1 can become operational to receive a sample to be assayed, and the device can start timing a second degeneration period P2 (steps 165, 166, 167). Also, preferably, an overall, measured, first degeneration period P1 is being stored (step 164).

For example, the device 1 can carry out a logic step: "When device is activated (for example application well is opened): activation time T1=timer (for example, from this moment on, the application well is exposed to outside air), STORE P1=T1, AND time second degeneration period P2".

Also in this case, the second degeneration period P2 may have passed a certain second expiration time ET2, which is being checked in a step 166, for example in the case that no sample is being applied at all, or too late. In that case, again, the device can perform a "fail"-step, and the assaying procedure can be halted. In case the second expiration time has not passed, and a sample is being applied in time, the device 1 can assay the sample, store the assay result and the respective second degeneration period P2 (step 168) and transmit the results (step 170).

For example, the device 1 can carry out the logic "DETECT IF sample is applied and WHEN sample is applied;

IF no sample applied at T=T1+Second Expiration time ET2: indicate FAIL (for example, the device warns the user that the device is no longer usable);

IF sample is applied at a sample application time T3 before time T1+Second Expiration time (T3<T1+ET2): assay sample".

An optional further step can comprise, for example: informing the user that the analysis has taken place. Also, the device 1 might correct the measurement for known degradation patterns, depending for example on expiration times/dates ET1, ET2, activation time T1 and sample application time T3. Also, preferably, after the assaying of a sample, the assaying result can be sent along with measured time periods. For example, a long time interval between device activation (time T1) and sample application (time T3) can indicate a large probability of contamination, and the length of this interval can be used as some measure of reliability.

In this way, the assaying can be carried out more reliably than in prior art methods. For example, the device 1 can monitor the application well(s) w to determine risk of contamination/chemical degradation. As follows from the above, in an embodiment, the device 1 may comprise a timer 25, and the application well w can be closed with a removable cover 29 that includes a sensor mechanism (not shown) coupled to the controller 8, to detect opening of the cover 29. For example, undesirable opening of an application well can take place, e.g. during transport (i.e. damage) or when the user has opened the application well (normal usage).

Also, in an embodiment, the device 1 can warn a user by turning on, for example, an indicator 26 (e.g. a red or green colored LED) next to a printed text, such as: "card is no longer usable, please throw card away"; "analysis has taken place, please return card to processing facility"; "analysis has taken place, please call phone number xyz to send results to processing facility"; and/or "test ready, please transmit test results".

As further extension of the functionality, the system can inform the user about the time remaining before a sample must be applied to the application well, for example via a display 38 and/or speaker 35. Also, to this end, the card may contain a number of period descriptions (like "one hour", "one day", "one week", etc) each with a LED. Initially, the LED next to the text "one week" lights up, and after 6 days the LED next to the text "one day" lights up, etc.

Another embodiment to improve the reliability, which can be applied in combination with the above, is a disposable assay device 1 that is provided with at least one user condition sensor 20 configured to detect at least one physical condition of a user of the device. Such a sensor is schematically indicated in FIGS. 1-3 as well, and can be configured in various ways, for example, comprising suitable monitoring or detecting means. As an example, during use (see FIG. 3), the user can carry the device 1, wherein at least one physical condition of the user U is being detected and/or monitored, before the device 1 is used or can be used to assay one or more samples.

For example, the user condition sensor 20 comprises a personal activity sensor, for example comprising an acceleration sensor, to measure personal activity when the device is being carried by the user during a personal activity measuring period.

Also, a suitable context sensor can be provided, comprising a temperature sensor 21 (see FIGS. 1 and 2) to measure the temperature of the environment of the device 1, wherein the device 1 is configured to allow the assaying of a sample only after a temperature detected by the temperature sensor 21 is within a predetermined temperature range, and/or to disallow the assaying of a sample in case the detected temperature is not in a predetermined temperature range. For example, the predetermined temperature range can be a range including room temperature (about 20° C.), a range between about 0-40° C., more particularly a range between about 10-30° C.

In a further embodiment, the assay device 1 can be configured to store each assay result in a memory unit 10 in combination with a user condition that has been detected by the user condition sensor 20. Thus, for example, assay results can be evaluated in combination with a detected user condition, to determine or estimate whether the assaying was performed in a desired manner and/or by a user having a desired user condition (for example a resting state).

For example, the device 1 (or at least its controller 8) can be configured to allow the assaying of a sample only after the at least one user condition sensor 20 has detected at least one physical condition of a user, and preferably only within a predetermined time period after such detection.

Figure 5:
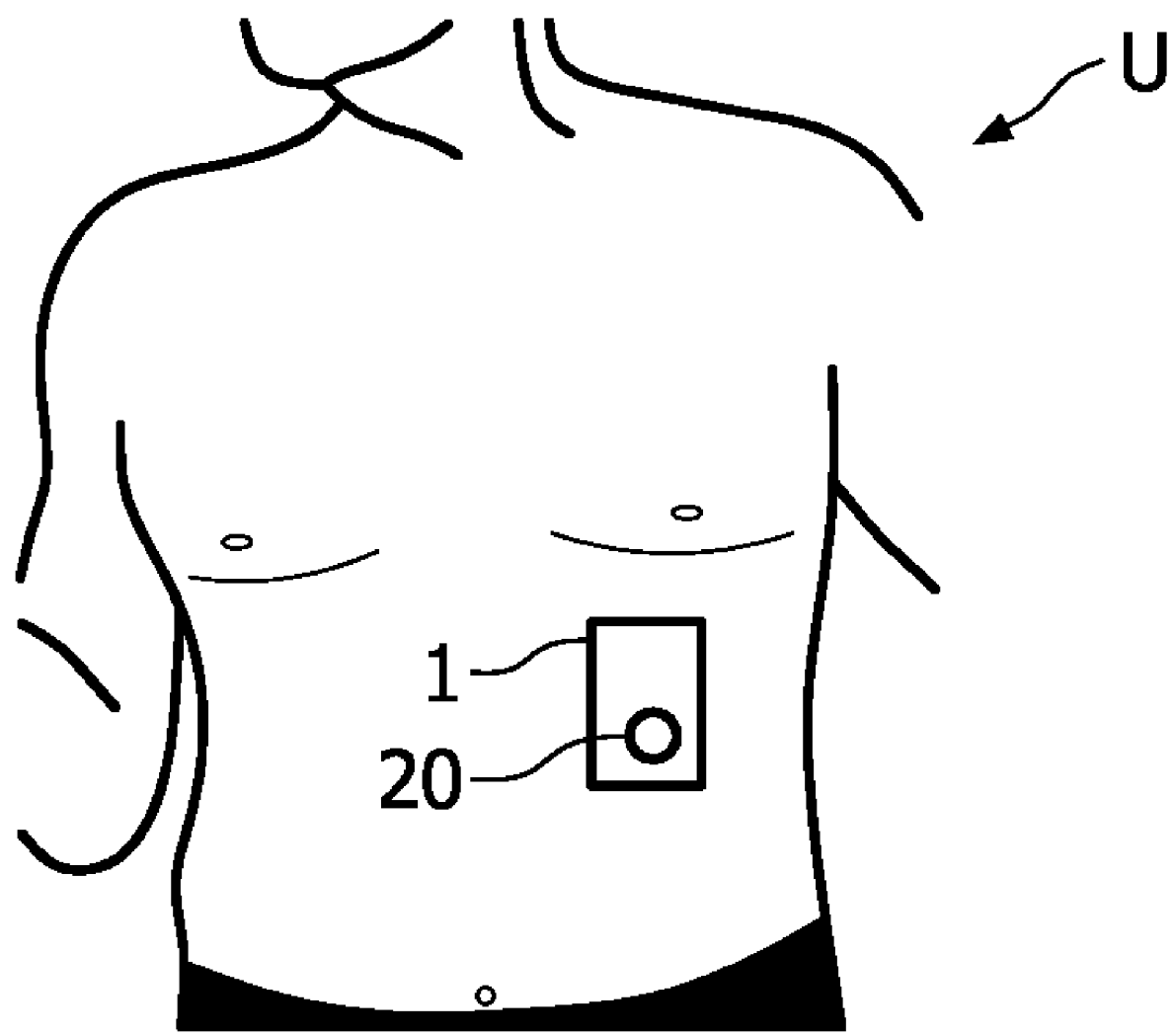
FIG. 5 shows the use of an embodiment, during a user condition measuring period.

The user condition sensor can be a heart rate sensor 20. For example, as is shown in FIG. 5, the device 1 can be configured to be carried in a heart rate detection position on a body part of a user U, wherein the heart rate sensor 20 is arranged to detect a heart rate-related signal emanating from the user body part, for example pressure pulses and/or acoustic signals, in case the device 1 is in the heart rate detection position. Moreover, the device can be configured to measure the heart rate during a heart rate measuring period to detect a lowest heart rate from respective measuring results and to store the lowest detected heart rate in a memory device 10.

As an example, the device 1 can be configured to be carried by a user during a certain measuring period, wherein the user condition sensor 20 is configured to measure at least one physical condition of the user during the measuring period, and to use the measuring results to determine or estimate when the user will be in a resting state during a subsequent period following the measuring period. Also, the device 1 can be configured to compare a detected physical user condition measurement result with a predetermined and/or stored user condition threshold value, particularly to detect if the user is in a desired assaying state (resting state) and/or to guide the user towards a desired assaying state.

In an embodiment, the device comprises a feedback generator, for example comprising the display and/or speaker, to provide feedback to a user U of the device 1 concerning measurement results provided by the mentioned user condition sensor 20. The device 1 can be configured to generate a message to guide a user of the device to assay one or more user samples, depending on measurement results provided by the mentioned user condition sensor 20.

Also, for example, for a correct measurement, it can be important to have the right subject in the right state, often a resting/relaxation state. In an embodiment comprising at least one user state monitor 20, the device 1 can simply check the user's (resting) state before measuring.

Besides, for example, in the case that the device 1 is provided with a heart rate sensor, according to an embodiment, the device 1 is placed at a position on the user's body such that the heart rate can be measured reliably (e.g. at the user's chest, see FIG. 5). Optimally, before the measurement takes place, the device 1 is calibrated by measuring the heart rate during a period of time, to determine the user's heart rate pattern and to be able to estimate the user's heart rate in a resting state. An algorithm to determine the user's heart rate in a resting state can be to measure the heart rate during 24 hrs and store the minimum value measured (which probably corresponds to sleeping). To cope with a slightly higher value in resting state during the day, this minimum value may be increased by e.g. 10%. Once the device 1 has been calibrated (i.e. after 24 hrs) and the user is in a resting state (i.e. the current heart rate <1.10*minimum value), the user may remove the device 1 from his body and do the actual measurement. The system informs the user about this condition by making a sound (or vibration), and by switching on a (green) LED next to a text like "user ready for measurement". The system stores the date & time at which the user removed the device 1 from his body.

Alternatively, the device 1 can be configured to track the changes in the detected heart rate, and can request that the user relaxes, and if no significant changes are detected for a period of time (presumably the heart rate drops initially as the user starts to relax), the user can be considered to be in a resting state.

In an embodiment, to start the measurement procedure, the user presses a "Start Test" button S or removes the cover from an application area w. The device 1 then preferably compares this moment with the date & time at which the user removed the device 1 from his body; if this period is short (e.g. 1 minute), the device 1 allows the user to do the test. However, if this period is too long, the user may no longer be in a resting state, and therefore the user is asked to measure his heart rate again (e.g. by switching on a (red) LED next to a text like "briefly hold the card on your chest"). If the current heart rate is too high, e.g. >1.0*minimum value, the device 1 can be configured to ask the user to rest for a few minutes, and to measure his heart rate again.

As follows from the above, instead of using a heart rate sensor or in addition to a heart rate sensor, a personal activity sensor 20 can be integrated in the device 1, or can be connectable thereto, and can be worn for example on the body (for example, it can be put in a pocket of clothing, because a connection to the skin is not necessary). The user activity sensor 20 can be used to check that the user does not perform any moderate or high activity actions for a sufficiently long period of time (e.g. 10 minutes), so that the device 1 can ensure that the user is in a resting state. This has the advantage that no calibration is necessary.

Besides, if the measurement may only be done in a certain environment temperature range, the card can be equipped with a mentioned temperature sensor 21. This sensor need not be calibrated: a (green) LED next to the text "card ready for measurement" indicates its fitness for use, whereas a (red) LED next to the text "please go to a warmer location" or "please go to a colder location" instructs the user to go to a location with the desired temperature.

In yet a further or another embodiment, the device 1 can comprise one or more user interaction buttons B, as in FIG. 2, and at least one fingerprint sensor 23 to detect a user's fingerprint after the fingerprint has been placed on the one or more buttons. Thus, a user can be identified, so that the device 1 can determine whether a desired user operates the device. Also, user identification can be carried out in case the device comprises a voice recognition and/or voice differentiation unit, particularly to provide or support user identification. During use, the device 1 can be sent, for example, to the home of the person that should do the test. To prevent that measurement data is associated with another person (e.g. the cards of 2 family members are exchanged, or a child uses his parent's card), a fingerprint sensor or microphone can be added. According to an embodiment, the fingerprint sensor is superposed on multiple-choice questions B on the card: by answering the questions, automatically a fingerprint is made. This fingerprint can be stored in the memory 10 of the device 1, and is preferably compared with a known fingerprint of the test person when device 1 arrives at a remote processing facility 30. In another embodiment, the person that has performed the test has to say his name in a microphone on the card 1 and this audio fragment is stored. One possibility is to compare this audio fragment with a pre-recorded audio fragment of the test person (which is available at the processing facility 30, e.g. because the test person has been phoned by the processing facility 30). Another possibility is to perform a more basic test: if the stored audio fragment contains the voice of a woman, whereas the device 1 had to be used by a man, it is very likely that something has gone wrong.

Another possibility is to have a human compare the stored voice to the actual voice of the test person. This can be useful in later stages when a sensitive measurement has to be confirmed (e.g. in a court case).

For example, measured context values before, during and after the assaying of one or more samples can be stored and transmitted back to the (central) processing center 30. In this way, the measurement procedure that the user actually followed and the environment in which it happened can be partially reconstructed. This can be used to judge whether the measured data is reliable enough, and whether the measured values need to be compensated for context influences.

An application of the invention can be to determine whether or not a patient has pre-diabetes or diabetes. However, testing for other diseases using body fluid samples may also benefit from this invention.

Advantageously, the assay system is, or is also, configured to carry out a relatively precise oral glucose tolerance test (OGTT), utilizing the assay device 1. This will be described in the following, referring to FIG. 6. The embodiment of FIG. 6 can be used in combination with above-described embodiments and/or embodiments shown in FIGS. 1-5.

For example, at least one eatable and/or drinkable product can be provided. In that case, the user can be guided to consume the eatable and/or drinkable product before and/or during using the device to assay a sample of the user. In a further embodiment, the eatable and/or drinkable product can contain glucose, wherein the assay device 1 is configured to test at least one blood sample for glucose. As an example, the product can be a sweet, winegum, a glucose containing beverage, or a different product. Besides, in this case, the disposable assay device 1 can be configured to assay at least two blood samples, for example by being provided with at least two application sample wells w (as in the embodiments of FIGS. 1-5). For example, a user guidance system can be available to guide the user of the device to test at least a second blood sample after elapse of a predetermined amount of time after testing a first sample. A clock or timer can be provided to measure the elapse of time after the user has applied a first blood sample to a respective application well. Preferably, degradation of one or more degradable substances can be monitored, as is explained above.

Figure 6:
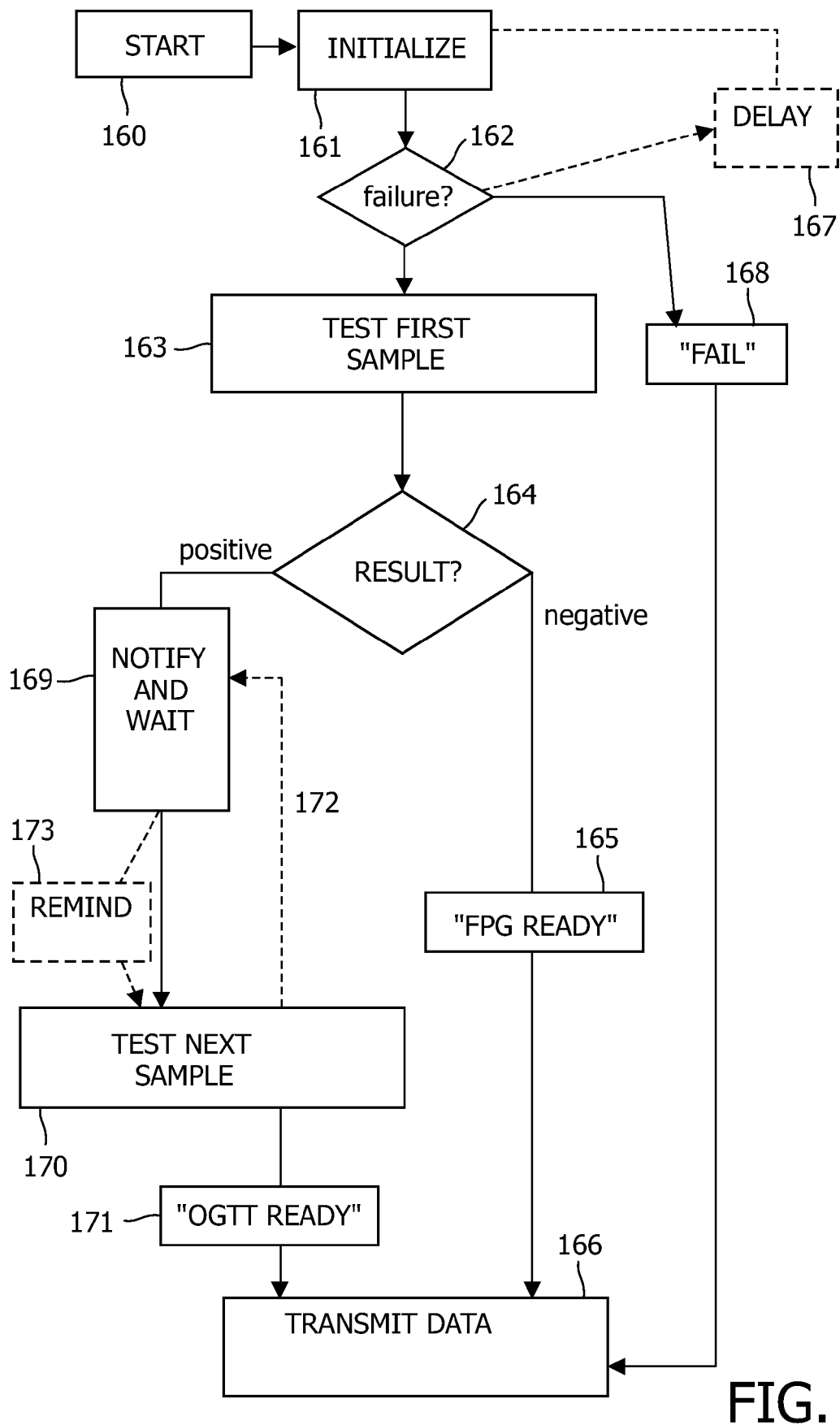
FIG. 6 shows a flow chart of another assay method.

The assay device 1 can be configured to generate a first test result relating to the assaying of the first sample. Also, the user can be guided to assay at least the second sample, depending on the first test result. For example, a second test can be carried out in case a first test result is "assay inconclusive", "assay failed", "device failure" or a similar result. However, preferably, a second test is carried out to turn an FPG test into an OGTT test. As an example, in case the first test result indicates that it is likely that the respective user has (pre-) diabetes, a second glucose test can be performed a predetermined time period after the first test, to provide an OGTT test, to verify the first test result and to provide a much more conclusive OGTT test result. For example, the assay device can be configured to carry out an oral glucose tolerance test, if desired. FIG. 6 depicts a flow-chart of a use of such a device.

In FIG. 6, the assaying of user blood can be started by the user (step 160), for example by pressing a specific "start test button" S, or giving a command in any other way to the assay device 1.

A subsequent initialization step 162 can involve asking the user questions Q (as in the embodiments relating to FIGS. 4-5). The outcome of this step 162 can be that the test is not suitable to the user. In that case, the device 1 can indicate "test is not suitable" in a fail-step 168, which test result can be transmitted to a data processing/remote receiving system 20 (step 166).

Alternatively (as indicated by broken lines), a result of the initialization step 162 can be that the user has to wait a certain amount of time before he may use the device. Such a delay is indicated by a delay-step 167. Also, during this step 162 it may be determined whether the user is in a fasting state (see above).

On the other hand, in case the initialization phase succeeds, a first user blood sample can be tested by the device 1 in a first blood test (step 163). For example, a well w of a removable assay part 3 can be used to receive a first blood sample.

Optionally, the user can be guided or instructed (for example by a mentioned user guidance system) to consume a mentioned, eatable and/or drinkable product, just before, during or after applying a user blood sample to an application well w of the assay device 1. Preferably, the consuming of the product is at such a time that it does not substantially change the outcome of the first blood test.

In case the first test is "negative" (i.e., chance of pre-diabetes or diabetes is unlikely), a "test ready" indication can be provided (for example "FPG ready", see step 165). Also, information or data relating to the test result can be transmitted to a processing facility 20 (step 166). For example, in the case that the user was in a fasting state just before taking his first blood sample, the first test result can be an FPG test result.

On the other hand, the device 1, or a user guidance system, may desire that a more accurate OGTT is performed. This can be the case, for example, when it had been found in the initialization step 162 that the user was not in a fasting state. Also, the OGTT test may be desired in case the first test result was positive (i.e., there is a likelihood of pre-diabetes or diabetes).

To perform the OGTT test, the device 1 (or user guidance system) can notify the user to wait a predetermined amount of time (step 169; for example 1 hour, 2 hours or a different period). The user can be instructed to take a second blood sample and test the sample, using a second application well w of the device 1 (for example a well w of another removable assay part 5), immediately after the lapse of the waiting period. Preferably, a reminder is provided by a user guidance system (step 173), for example via an alarm of the device 1 or via a call from a remote call center, that the waiting period is about to lapse and/or has just lapsed. Then, a second blood sample can be applied and tested (step 170), using the device 1. Thus, an oral glucose tolerance test can be carried out. Optionally, after the testing of a second blood sample, one or more blood samples can be tested after predetermined waiting periods (step 172). Preferably, the device 1 measures the amount of time that has lapsed between the application of the various blood samples to respective application wells, and stores the lapsed time period(s), or stores the times that the samples were applied to the device 1.

After completion of the testing of the at least first and second blood samples, a test ready signal can be provided (for example "OGTT ready", see step 171), and resulting test information can be transmitted in a suitable manner (step 166).

An advantage of the OGTT test is that it is much more reliable than the FPG test. In this way, for example, the assay device 1 can at least perform, or try to perform, a relatively fast FPG test on a user blood sample. Depending on the outcome of this test, or depending on the user's condition, the test can be changed into the OGTT test. In the latter case, the FPG test can simply be used as part of the OGTT test.

Although the illustrative embodiments of the present invention have been described in greater detail with reference to the accompanying drawings, it will be understood that the invention is not limited to those embodiments. Various changes or modifications may be effected by one skilled in the art without departing from the scope or the spirit of the invention as defined in the claims.

It is to be understood that in the present application, the term "comprising" does not exclude other elements or steps. Also, each of the terms "a" and "an" does not exclude a plurality. Also, a single processor or other unit may fulfill functions of several means recited in the claims. Any reference sign(s) in the claims shall not be construed as limiting the scope of the claims.

For example, in an embodiment, the present assay device 1 can be configured to be carried by a user during a certain measuring period, wherein the user condition sensor is configured to measure at least one physical condition of the user during the measuring period, and to use the measuring results to determine or estimate when the user will be in a resting state during a subsequent period, following the measuring period.

Also, in an embodiment, the present assay device can be configured to compare a detected physical user condition measurement result with a predetermined and/or stored user condition threshold value, particularly to detect if the user is in a desired assaying state (resting state) and/or to guide the user towards a desired assaying state.

In a further embodiment, the device can comprise a feedback generator to provide feedback to a user of the device concerning measurement results provided by the mentioned user condition sensor.

Besides, in case the present assay device 1 is configured to generate a message, it can be advantageous to guide a user of the device to assay one or more user samples, depending on measurement results provided by the mentioned user condition sensor.

In an embodiment, the above-described assay device 1 can comprise one or more user interaction buttons and at least one fingerprint sensor to detect a user's fingerprint after the fingerprint has been placed on the one or more buttons.

Also, according to an embodiment, the assay device can comprise a voice recognition and/or voice differentiation unit, particularly to provide or support user identification.

Besides, advantageously, there can be provided an assay system comprising at least one device according to the present invention, and at least one receiving system (30) which is configured to receive assay data or information, the assay data or information relating to, being based on and/or comprising one or more assay results of the assay devices (1) and/or comprising information that the assaying has failed.

The invention claimed is:

1. A disposable assay device to assay one or more samples, the disposable assay device comprising:
    at least one sample application area for receiving the one or more samples;
    a controller for performing the assay of the one or more samples and forming assay data;
    a transmitter for transmitting the assay data to a remote receiving system; and
    one or more assay context sensors to monitor one or more assay context factors,
    wherein the at least one sample application area includes a first area for receiving a first sample and a second area for receiving a second sample for performing a sequence of measurements using the first sample and the second sample, and wherein a carrier of the controller is between the first area and the second area.

2. The disposable assay device of claim 1, further comprising one or more degradable assaying substances having a degradation of which is time-dependent, and wherein the controller monitors the degradation of the one or more degradable assaying substances, the controller including a timer to time at least one degradation period of the one or more degradable assaying substances.

3. The disposable assay device of claim 2, wherein the controller and the timer cooperate to measure at least a first degradation period during which the device is in a non-operating state where the one or more degradable assaying substances are not available to receive the one or more samples, the disposable assay device having an operating state when the one or more degradable assaying substances are available to receive the one or more samples.

4. The disposable assay device of claim 3, wherein the controller and the timer cooperate to measure at least a second degradation period which is a time between activation of the disposable assay device and receiving of the one or more samples by the one or more degradable assaying substances, and wherein the controller takes into account both the first degradation period and the second degradation period to determine an overall degradation of the one or more degradable assaying substances.

5. The disposable assay device of claim 1, wherein the controller disallows use of the disposable assay device in case a monitored assay context factor is equal or greater than a predetermined threshold.

6. The disposable assay device of claim 1, further comprising an indicator to indicate a time remaining for a user of the disposable assay device to use the disposable assay device to assay the one or more samples.

7. The disposable assay device of claim 1, wherein the controller detects activation of the disposable assay device and detects application of the one or more samples to the disposable assay device, and stores at least one of a time and a date of the activation of the disposable assay device, as well as at least one of a time and a date of the application of the sample.

8. The disposable assay device of claim 1, wherein the one or more assay context sensors comprises a personal activity sensor comprising an acceleration sensor to measure personal activity when the disposable assay device is being carried by a user of the disposable assay device during a personal activity measuring period.

9. The disposable assay device of claim 1, wherein the one or more assay context sensors comprises a temperature sensor to measure a temperature of an environment of the disposable assay device, wherein the controller allows the assay of the one or more samples only after a temperature detected by the temperature sensor is within a predetermined temperature range, and disallows the assay of the one or more samples in case the detected temperature is not in the predetermined temperature range.

10. The disposable assay device of claim 1, further comprising a memory unit to store each assay result in the memory unit in combination with assay context information.

11. The disposable assay device of claim 1, wherein the one or more assay context sensors comprises a heart rate sensor to be carried in a heart rate detection position on a body part of a user of the disposable assay device, wherein the heart rate sensor detects a heart rate-related signal emanating from the body part when the disposable assay device is in the heart rate detection position.

12. The disposable assay device of claim 11, wherein the heart rate sensor measures the heart rate during a heart rate measuring period, to detect a lowest heart rate from respective measuring results and to store the lowest detected heart rate in a memory device.

13. The disposable assay device of claim 1, further comprising a memory unit, wherein the controller provides a testing signal during at least part of a first time period, when the disposable assay device has not received a first sample, and during at least part of a second time period, when the device has received the first sample; wherein the memory unit stores the testing signal during the first time period and the second time period, in combination with a respective testing signal generation time.

14. The disposable assay device of claim 13, wherein the at least one sample application area includes at least one substance which is responsive to a specific analyte to be searched, and the testing signal is dependent on at least one of an amount and a condition of the at least one substance.

15. The disposable assay device of claim 1, wherein the first area and the second area are independently removable from the carrier of the controller.

16. The disposable assay device of claim 1, further comprising at least one user condition sensor configured to detect at least one physical condition of a user of the disposable assay device.

17. The disposable assay device of claim 1, wherein the controller detects removal of the at least one sample application area from a carrier of the controller and stores time of the removal in a memory.

18. The disposable assay device of claim 1, wherein the assay data includes measurement values and respective times when the measurement values are obtained to form a testing signal as a function of time.

19. The disposable assay device of claim 1 wherein, based on at least one factor detected by the one or more assay context sensors, the controller automatically adjusts at least one of an expiration time for using the disposable assay device and an expiration time for performing the assay after reception of the one or more samples by the at least one sample application area.

20. The disposable assay device of claim 1 wherein the at least one factor includes temperature.

* * * * *